United States Patent [19]

Fried et al.

[11] Patent Number: 4,629,015

[45] Date of Patent: Dec. 16, 1986

[54] WEIGHT MONITORING SYSTEM

[75] Inventors: Peter Fried; Burt L. Swersey, both of Scarsdale, N.Y.

[73] Assignee: Cobe Asdt, Inc., Elmsford, N.Y.

[21] Appl. No.: 675,833

[22] Filed: Nov. 28, 1984

[51] Int. Cl.⁴ .................... G01G 23/22; G01G 23/32; G01G 19/00; A61M 31/00
[52] U.S. Cl. .................................... 177/25; 177/178; 177/245; 604/66; 128/DIG. 13
[58] Field of Search ................. 177/25, 177, 178, 50, 177/245; 604/66; 128/DIG. 13

[56] References Cited

U.S. PATENT DOCUMENTS 4,301,879 11/1981 Dubow ............................ 177/5
4,318,447 3/1982 Northcutt ....................... 177/25

FOREIGN PATENT DOCUMENTS 161511 10/1982 Japan .......................... 177/50

Primary Examiner—George H. Miller, Jr.
Attorney, Agent, or Firm—Kenyon & Kenyon

[57] ABSTRACT

The weight monitoring system provides a visual read-out to compare an actual weight change in a patient undergoing a change of weight treatment against the elapsed time of treatment. In one embodiment, the actual weight loss is displayed in bar form against the elapsed time also in bar form. In a second embodiment, the read-out uses a display screen for graphically displaying a chronological sequence of differences between a programmed weight change and an actual weight change.

The monitoring system can be used to automatically control a dialysis unit or may provide readings which permit a manual adjustment in a dialysis unit.

16 Claims, 4 Drawing Figures

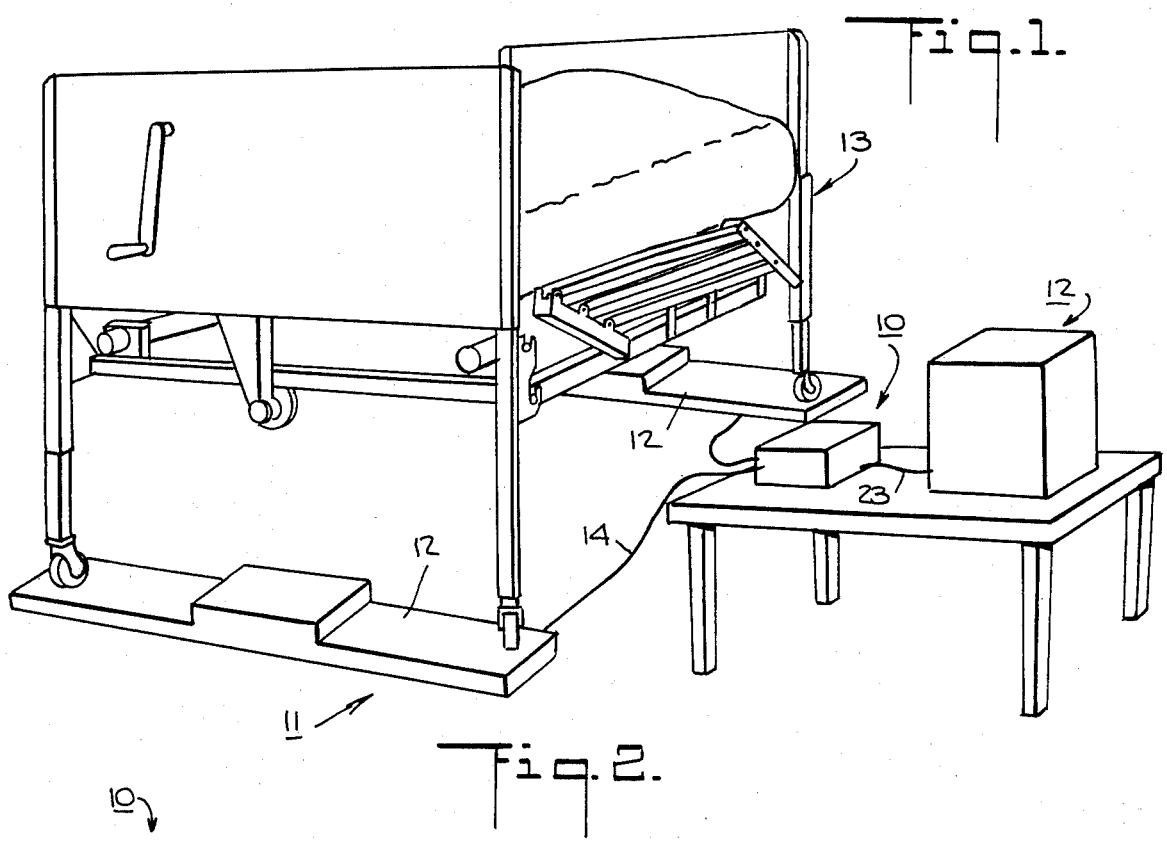
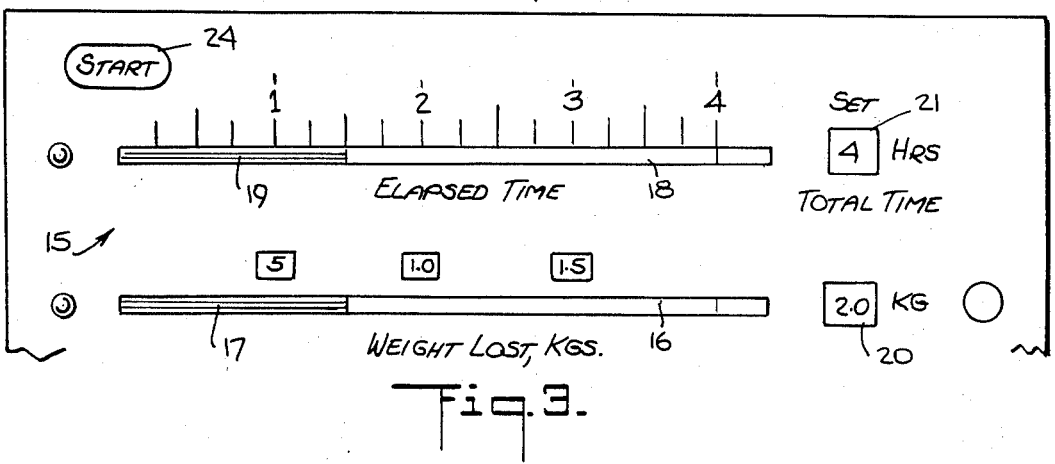
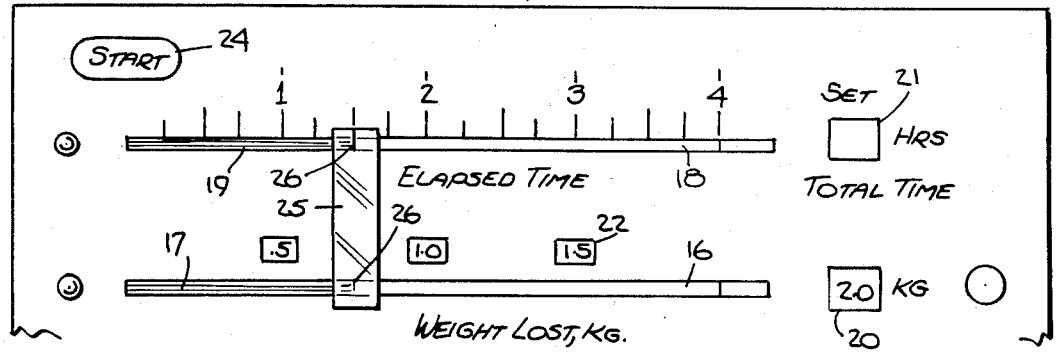

WEIGHT MONITORING SYSTEM

This invention relates to a weight monitoring system. More particularly, this invention relates to a weight monitoring system for a scale. Still more particularly, this invention relates to a weight monitoring system for use with a patient undergoing a dialysis treatment.

As is known, there are many types of treatment which require that a patient undergo a weight loss or a weight gain during treatment. For example, in the case of a dialysis treatment, it is generally required that a patient lose a predetermined amount of weight over a given period of time. In this regard, a dialysis patient is usually subjected to a dialysis treatment wherein his blood is continuously passed through a dialysis machine in order to remove water and chemicals from the blood stream.

In the past, patients were connected to dialysis machines for periods of time which were considered to be sufficient to remove sufficient water and chemicals, for example for eight or more hours of time. However, these treatments required the patients to be confined to a fixed location such as a bed for excessive periods of time.

In more recent times, dialysis treatments have been carried out over shorter periods of time, for example over a four hour period during which a predetermined weight loss is obtained. In these cases, the period of time is usually established as the minimum for removing water and chemicals from a patient so as to bring the patient to a weight which has been previously determined as his desired weight. The amount of weight loss is presumed to be equivalent to the amount of water and chemicals which have to be removed from his body.

The dialysis machines which have been available to dialysize a patient over a four hour period have usually been programmed so as to remove a certain rate of fluids over a period of time. However, the membrane or filtering equipment which has been used in these machines to withdraw fluids from a blood stream can vary in the rate of removal not only during treatment but also from one treatment to the next should the membrane or filters be of a reusable type. To ensure that a patient is losing weight at an appropriate rate, an attendant ususally checks the weight of the patient from time to time during treatment to determine whether or not the patient will reach the desried weight at the end of the treatment time. For example, if the attendant determines that the weight loss is too slow, the dialysis machine is adjusted to increase the rate of fluid withdrawal. If the weight loss appears to be too fast, the machine is slowed. However, such a technique requires several readings to be made by an attendant over the time period in order to make a determination as to the weight loss in the patient. Further this can be complicated should the patient consume any foods or liquids during treatment since this would increase the patient's weight. Also, should the patient pick up a book or other reading material during a weighing operation, such might also give a spurious weight reading.

Where dialysis treatment is carried out over a short period of time, use has frequently been made of a scale and chair arrangement wherein the patient is seated in a chair of comfortable contour with the chair, in turn, mounted on a scale platform so that weight readings can be obtained of the patient from time to time.

In summary, the techniques which have been employed to date for monitoring the weight loss of a dialysis patient have been tedious and time consuming. Further, in many cases, the techniques have not been accurate.

Accordingly, it is an object of the invention to accurately monitor the weight loss of a patient undergoing a dialysis treatment.

It is another object of the invention to be able to change the rate of fluid withdrawal from a dialysis patient during treatment in order to secure a programmed rate of weight change.

It is another object of the invention to provide a relatively simple monitoring system for monitoring the weight loss of a patient undergoing a change of weight treatment.

It is another object of the invention to provide a monitoring system which provides a visual readout of changes in a programmed rate of fluid withdrawal in a dialysis patient.

It is another object of the invention to provide a method of monitoring a weight loss of a patient in a simple manner.

Briefly, the invention provides a weight monitoring system and a method of monitoring weight.

The weight monitoring system is particularly adapted for use with a scale and includes a means for generating a signal corresponding to a weight change of a load on the scale over a period of time, a second means for generating a signal corresponding to the lapse of time within the period of time and a comparison means for comparing the signals with each other over the period of time. In one embodiment, the comparison means includes a visual read-out means for displaying the signals. For example, this visual read-out means may be in the form of a comparison means which includes a linear display for chronologically displaying an actual change in weight of the load at a given time in bar form and a separate linear display parallel to and adjacent the first linear display for continuously displaying the elapsed time in bar form. This permits a visual comparison of the actual change in weight at a given point in time so as to determine if the weight is progressing correctly.

In another embodiment, the weight monitoring system employs a first means for receiving an actual weight signal from a weighing scale, a second means for generating a signal corresponding to a desired program weight, a comparator connected to the two means for receiving and comparing the actual weight signal and the programmed weight signal in order to produce an error signal in response to a difference therebetween and a visual read-out means for displaying a chronological sequence of these error signals. For example, the first means may be in the form of an analog to digital convertor for converting an analog signal from the scale which is indicative of actual weight into a digital signal. In this case, the comparator is in the form of a digital comparator.

The read-out means may also include a display screen for graphically displaying a chronological sequence of the error signals. This is of importance since the read-out means may then provide a trend indicator of the deviations of the actual weight from the programmed or ideal weight over time. For example, if an attendant notes that a sequence of error signals are of the same value over a given period of time, no adjustment need be made in the treatment. On the other hand, if a sequence of error signals indicates a trend to increasing errors, a change can be made in the treatment so as to reduce the values of subsequent error signals.

The weight monitoring system is particularly useful in monitoring the weight of a dialysis patient. For example, the monitoring system can be connected to and between a scale which weighs the patient and produces an output signal corresponding to the actual weight and a dialysis unit which includes means for controlling the rate of withdrawal of the fluids from the patient. During use, the dialysis unit can be programmed in known manner to withdraw fluids from the patient at a predetermined rate so as to achieve a certain nominal or desired weight of the patient at the end of a given period of time. The monitoring system is then able to compare the actual weight of the patient on the scale with the programmed weight for that instant of elapsed time to obtain and display any difference between the weights in an automatic manner. By displaying a chronological sequence of error signals along with the magnitude of each, an attendant can quickly and visually determine a trend in the treatment and make adjustments in the dialysis machine if necessary.

In order to obtain a signal corresponding to the programmed weight for the patient, the monitoring system includes a programmer which receives a signal corresponding to the desired weight loss for a patient as well as a signal corresponding to the desired time of treatment. With another signal being directed to the programmer which corresponds to the starting weight of the patient and with another signal corresponding to the elapsed time of treatment, the programmer can be suitably programmed so as to produce a signal equal to the starting weight less the amount of weight which should have been lost at the elapsed time. This resulting signal is then used as the programmed weight signal for comparison in the comparator.

In addition to obtaining a visual read-out of a sequence of error signals, the error signals may also be used to control the rate of withdrawal of fluids in the dialysis unit. In this respect, the monitoring system would be connected to the control means in the dialysis unit in order to automatically adjust the control means in response to an error signal. Furthermore, the control means may be continuously adjusted by a series of error signals.

These and other objects and advantages of the invention will become more apparent from the following detailed description taken in conjunction with the accompanying drawings wherein:

FIG. 1 illustrates a schematic view of a weight monitoring system employed with a dialysis unit and a scale for receiving a bed;

FIG. 2 illustrates a front view of a visual comparison means of the monitoring system in accordance with the invention;

FIG. 3 illustrates a modified view of the comparison means of FIG. 2; and

Figure 4:
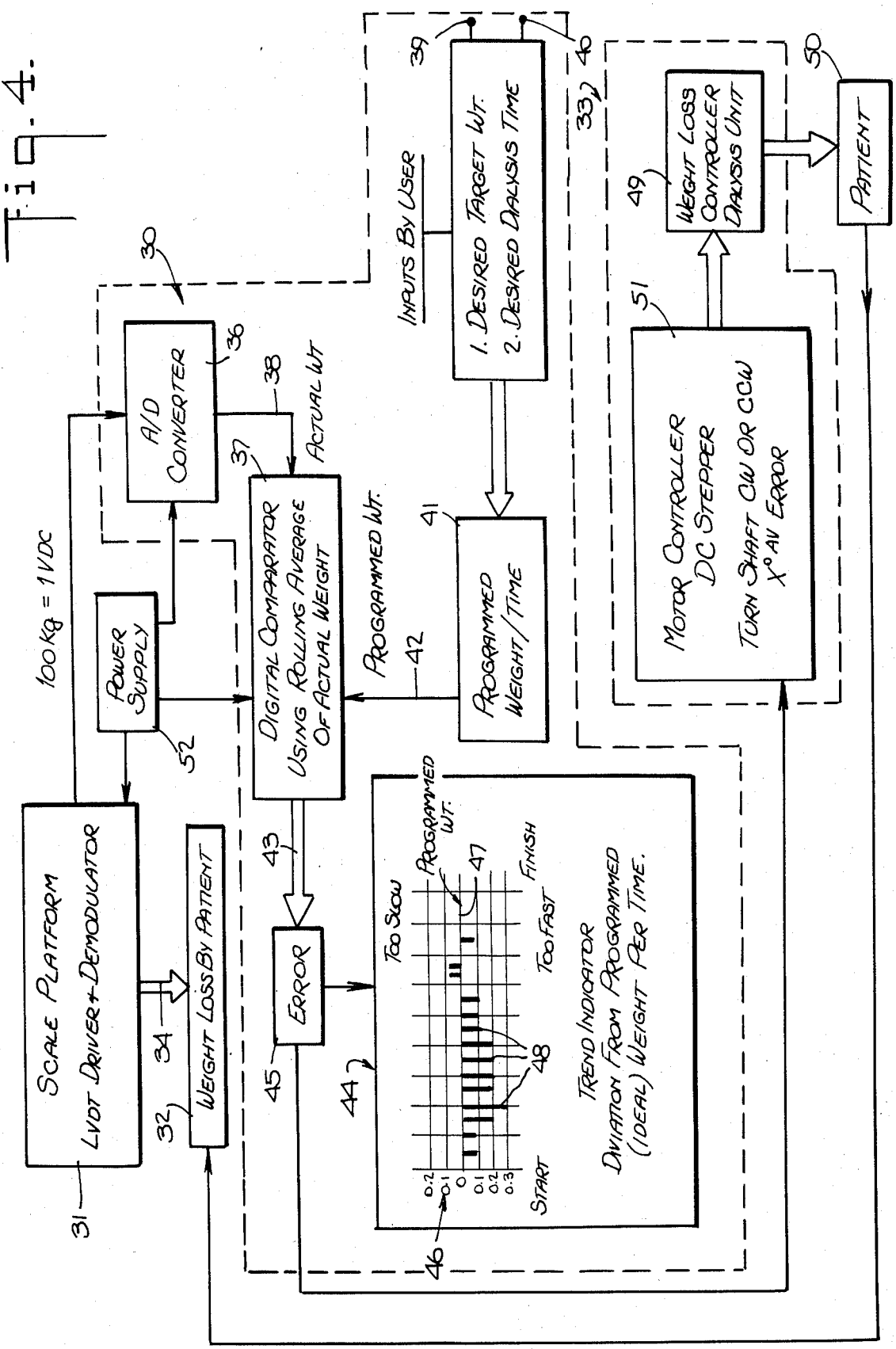
FIG. 4 illustrates a diagramatic view of a monitoring system in combination with a scale and a dialysis unit.

Referring to FIG. 1, the weight monitoring system 10 is employed with a scale 11 and a dialysis unit 12. As indicated, the scale 11 is of a type such as described in U.S. Pat. No. 4,281,730 which is suitable for weighing a bed-ridden patient. To this end, the scale 11 includes two platforms 12 for receiving the head and foot, respectively of a bed 13. The platforms 12 are, in turn, electrically connected by suitable lines 14 to the monitoring system 10 in order to deliver signals thereto indicative of the weight of a load on the scale 11. For example, the weight signals may be emitted in the form of a DC signal such that 100 kilograms will produce a DC signal of 1.000 volts.

Referring to FIG. 2, the weight monitoring system 10 includes a suitable means for generating a signal corresponding to the weight change of a load on the scale 11. To this end, any suitable circuit may be provided to receive the weight signal from the scale 11 and to convert the signal, from analog to digital form. In addition, the circuit may be actuated at predetermined intervals of time in order to provide a chronological sequence of readings.

The monitoring system 10 is also provided with a means for generating a signal corresponding to the lapse of time within a given period of treatment time. To this end, any suitable timing circuit can be used to generate the signal. Again, the signal may be of digital form.

The monitoring system 10 also has a comparison means as indicated in FIG. 2 for comparing the weight change signal with the lapse of time signal. As indicated, the comparison means includes a visual read-out means 15 for displaying the signals. Specifically, the comparison means includes a first linear display 16 for chronologically displaying the actual change in weight of a load on the scale 11 at a given time in bar form 17 as well as a second linear display 17 parallel and adjacent to the first display 16 in order to continuously display the elapsed time signal in bar form 19.

The monitoring system also has suitable controls for receiving an input signal corresponding to a desired weight change for a load on the scale 11 as well as a corresponding read-out 20 for displaying the desired weight change, for example in kilograms. Further, the monitoring system has a suitable input for receiving a signal corresponding to the programmed time of treatment as well as a corresponding read-out 21 for displaying the time, for example in hours. As indicated in FIG. 3, the linear display 16 for the actual weight change can be provided with suitable read-out indicators 22 which are programmed to give certain percentages of the programmed weight change. For example, as indicated, for a 2.0 kilogram change the three indicators 22 would show program signals corresponding 0.50 kilograms, 1.0 kilograms and 1.5 kilograms. The end of the linear display 16 would actually extend beyond a point which would be equivalent to a 2.0 kilogram position. In a similar manner, the elapsed time display 18 is provided with indicia to indicate elapsed time.

Referring to FIG. 1, the dialysis unit may be of any suitable known type which can be connected to a patient for withdrawing fluid from the blood stream of a patient on the bed 13. As is known, such dialysis units include control means for controlling the rate of withdrawal of fluids from the blood stream of a patient. As indicated in FIG. 1, the monitoring system 10 can be connected with the dialysis unit 12 via an electrical line 23 for automatically controlling the rate of withdrawal effected by the dialysis unit 12.

In use, the desired weight of a patient to be treated is first determined. Thereafter, the patient is positioned on the bed 13 and an actual weight is determined via the scale 11 and a suitable read-out (not shown). The difference between the two weights is then used as the desired weight loss to be obtained during dialysis treatment. This information is then fed into the monitoring system and displayed on the read-out 20. In addition, the time of treatment is determined and this information is also inputted to the monitoring system 10 and displayed on the read-out display 21. The dialysis unit 12 can then be connected in the usual fashion and treatment started. At the same time, the monitoring system 10 would be activated, for example via a suitable start switch 24.

As the patient is being treated, the weight of the patient would gradually reduce in a continuous manner. If the monitoring system 10 is programmed to function at predetermined time intervals, an actual weight signal is obtained from the scale 11 at these intervals of time and a corresponding signal is generated within the monitoring system 10 and displayed in bar form 17 on the linear display 16. In this regard, the linear display 16 shows only the change in weight, i.e. a loss in weight value. At the same time, the monitoring system generates a signal indicating the elapsed time and also displays an elapsed time signal 19 on the linear display 18.

Should the patient be losing weight at the desired programmed rate, the displayed bar signal 17,18 would be of equal length. For example, if the treatment time were 4 hours and the desired weight loss was 2.0 kilograms, at an elapsed time of 1.5 hours, the weight loss should be 0.75 kilograms.

If the actual weight loss at a given period of time is not equal to the desired weight loss of that period of time, the bar 17 would not be of equal value to the elapsed time bar 19. Depending on whether the weight loss bar 17 is ahead of or behind the elapsed time bar 19, an attendant can make an adjustment in the dialysis unit 12 to slow down or speed up the rate of fluid withdrawal from the patient so as to coordinate the bars 17, 19.

Referring to FIG. 3, wherein like references characters indicate like parts as above, the rate monitor 10 may also be provided with an indicator 25 which is able to slide along the linear display 16,18 so as to aid in visually aligning the extents of the bars 17,19 with each other. As indicated, the indicator 25 may be of transparent material with suitable indicia marks 26 for alignment purposes.

The rate monitoring system 10 may also be constructed to emit a suitable signal via the line 23 to the dialysis unit 12 to indicate that the desired weight loss has been obtained.

Referring to FIG. 4, the rate monitoring system may also be connected between a scale 31, for example of the type described in U.S. Pat. No. 4,023,633 wherein a patient can be seated in a chair (not shown), such as a lounge chair, which is, in turn, mounted on the scale 31. In such a situation, the monitoring system 30 can be positioned adjacent to the chair and provided with a read-out means 32 for an instanteous read-out. For example, with a patient seated in the chair initially, the total weight of the patient before treatment can be recorded on the read-out means. This weight may then be tared out, for example at the scale or at the read-out, so that a zero reading or other suitable standard is obtained. Thereafter, as treatment progresses, any fluctuations in the weight of the patient from the standard can be monitored in the monitoring system 10.

As also indicated in FIG. 4, the monitoring system 30 is connected to a dialysis unit 33 to automatically adjust the dialysis unit 33.

As indicated in FIG. 4, the scale 31 is provided with suitable means such as an LVDT driver and demodulator for generating a signal indicative of the weight loss by a patient. This signal can then be directed via a suitable line 34 to the read-out 32. At the same time, the signal can be emitted via a line 35 to the monitoring system 30. For example, the signal can be emitted so that a 0.001 volt signal value corresponds to 0.1 kilograms.

The monitoring system 30 has a means in the form of an analog to digital converter 36 for receiving the actual weight signal from the scale 31 via the line 35. The converter 36 then generates a corresponding signal for delivery to a comparator 37 which is connected thereto via a suitable line 38.

In addition, the monitoring system 30 has an input means 39 for receiving a signal corresponding to a desired weight change and a second input means 40 for receiving a signal corresponding to a period of time over which the weight change is to occur. These inputs 39, 40 are connected to a programmer 41 within which the information received is able to emit a programmed rate signal (PR) via a line 42 to the comparator 37.

For example, obtaining the starting weight (SW) of a patient and subtracting the desired weight (TW), i.e. the dry target weight, the desired weight loss (TL) can be obtained by a simple substraction. Further, the desired rate (DR) of weight loss, for example in grams per hour can be obtained by dividing the desired weight loss (DL) by the time of dialysis treatment (DT) multiplied by 1000. Again, this calculation can be carried out within the programmer.

The programmed weight (PR) can be obtained by subtracting from the starting weight (SW) the desired weight loss (DL) for the elapsed time (ET) during the treatment time (DT). Again, this can be suitably programmed within the programmer 41.

The comparator 37 is of digital type and is connected to the convertor 36 and the programmer 41 in order to receive an compare the actual weight signal delivered via the line 38 and the programmed weight signal delivered via the line 42 and to produce an error signal via a line 43 in response to a difference between the actual weight signal and the programmed weight signal. This error signal can be produced at periodic intervals of time during treatment or can be produced on a continuous basis.

The monitoring system also has a visual read-out means 44 for displaying a chronological sequence of the error signals. In this regard, the read-out means 44 is connected to the line 43 and is suitably programmed to visually indicate the value of the error signal at given intervals of time during the treatment program. A suitable display 45 is also provided to visually indicate the value of the error signal emitted via the line 43.

As indicated in FIG. 4, the read-out means 44 includes a display screen 46 for graphically displaying a chronological sequence of the error signals. As indicated, the graph shows a time line 47 on an X-axis while the error signals are emitted at predetermined intervals of time at values which are measured along a Y-axis. In the illustrated display, a chronological sequence of error signals 48 are illustrated which are of different values. For example, the first two error signals are of the same value. This indicates that the weight of the patient differs from the programmed weight by the same amount. The next two succeeding signals indicate that the difference is increasing while the next four signals indicate that the differences have decreased.

The pattern of error signals indicated in FIG. 4 shows by negative values that the patient is initially losing weight at a faster rate than the programmed or desired rate but that the patient's weight is gradually brought back to the programmed rate to finish at the desired weight. As such, the visual display provides a trend indicator by which an attendant can visually determine whether or not a patient is progressing along at a suitable rate equal to or close to the rate of programmed decrease. At the end of a treatment, the graph can be retained for historical purposes.

As indicated in FIG. 4, the error signal can be emitted via the line 43 directly to the dialysis unit 33. In this respect, the dialysis unit 33 includes a means in the form of a controller 49 for controlling the rate of withdrawal of fluids from a patient 50. In addition, the controller 49 is controlled by a motor controller 51 such as a DC stepper motor. The error signal can be emitted over the line directly to the motor 51 so as to speed up or slow down a motor and, thus, the controller 49 so as to increase or decrease, respectively, the rate of withdrawal of fluids from the patient 50. Alternatively, the motor can be adjusted manually by an attendant without using automatic controls.

In use, a patient 50 can be placed on the chair which is mounted on the scale 31 and an initial weight reading taken. At the same time, the desired target weight (DW) and the desired dialysis time (DT) can be fed into the programmer 41 of the monitoring system 30. Once activated, the monitoring system 30 can then monitor the actual weight losses which occur against the programmed weight throughout the treatment time while producing a visual display of any differences.

As indicated in FIG. 4, a suitable power supply 52 is connected to the scale 31 and the convertor 36 and comparator 37 of the monitoring system 30.

The method of monitoring the weight of a patient undergoing a change in weight treatment comprises the simple steps of generating a first signal corresponding to an actual change in weight of the patient at at least one point in time during the treatment, generating a second signal corresponding to an elapsed of time of the treatment and displaying the signals to obtain a visual comparison of the change in weight relative to the elapsed time. Such a method can be readily carried out in the embodiment as illustrated in FIGS. 1 to 3. In this respect, the signals can be displayed in bar form and in parallel relation and may also be continuously displayed during the time of treatment.

Alternatively, the method of monitoring the weight of a patient may be carried out in a manner as indicated in FIG. 4. In this respect, a first signal is generated corresponding to an actual weight of the patient at predetermined intervals of time during treatment. This signal is then compared with a second signal corresponding to a desired programmed weight for the patient at each interval of time so as to obtain an error signal in response to a difference between the two received signals. This error signal can then be displayed at each interval of time, for example graphically and in chronological sequence.

The invention thus provides a monitoring system and a method of monitoring which is relatively simple and which can continuously indicate to an attendant whether or not a patient is losing weight at a programmed weight.

Further, the invention provides an embodiment wherein a dialysis unit or the like can be adjusted so as to adjust the rate of withdrawal of fluids from a patient in dependance upon the programmed weight actually obtained.

Further, the invention permits a patient being treated to consume fluids or food or to pick up a book. In these cases, an unusual error signal would be produced on the read-out display, for example as indicated in FIG. 4. An attendant can thereafter tare out the weight which has been added or, in the case of food, may speed up the dialysis treatment in order to reduce the weight of the patient by the amount fluids or food which have been consumed.

What is claimed is:

1. A weight monitoring system for a scale, said system comprising
    first means for generating a signal corresponding to a weight change of a load on the scale over a period of time;
    second means for generating a signal corresponding to the lapse of time within said period of time; and
    a comparison means for comparing said first signal with said second signal over said period of time, said comparison means including a visual read-out means for displaying said signals, a first linear display for chronologically displaying an actual change in weight of the load at a given time in bar form and a second linear display parallel to and adjacent said first linear display for continuously displaying the elapsed time in bar form.

2. A weight monitoring system for a scale, said system comprising
    first means for receiving an actual weight signal from a weighing scale;
    second means for generating a signal corresponding to a desired programmed weight, said second means including a first input means for receiving a signal corresponding to a desired weight change, a second input means for receiving a signal corresponding to a period of time for the weight change and an output means for delivering the programmed weight signal in correspondence to a desired weight at a point in said period of time;
    a comparator connected to said first means and said second means for receiving and comparing the actual weight signal and said programmed weight signal to produce an error signal in response to a difference therebetween; and
    a visual read-out means for graphically displaying a chronological sequence of said error signals.

3. A weight monitoring system as set forth in claim 2 wherein said first means is an analog to digital convertor for converting an analog signal indicative of actual weight into a digital signal.

4. A weight monitoring system as set forth in claim 3 wherein said comparator is a digital comparator.

5. A weight monitoring system as set forth in claim 2 wherein said read-out means includes a display screen for graphically displaying a chronological sequence of said error signals.

6. A system as set forth in claim 1 which further includes a slider disposed over said linear displays and having an indicator line thereon for comparing the linear extent of said bar forms.

7. In combination,
    a scale for weighing a patient undergoing a change in weight treatment, said scale having means for emitting an output signal corresponding to an actual weight of the patient; and
    a weight monitoring system connected to said scale to receive said actual weight signal, said system including second means for generating a signal corresponding to a desired programmed weight for the patient at a given time during the treatment, said second means including a first input means for receiving a signal corresponding to a desired weight change, a second input means for receiving a signal corresponding to a period of time for the weight change and an output means for delivering the programmed weight signal in correspondence to a desired weight at a point in said period of time.

8. The combination as set forth in claim 7 which further comprises
a dialysis unit for withdrawing fluids from the patient on said scale, said dialysis unit including means for controlling a rate of withdrawal of fluids from the patient.

9. The combination as set forth in claim 8 wherein said monitoring system is connected to said means of said dialysis unit to automatically adjust said means in response to said error signal to vary the rate of withdrawal.

10. The combination as set forth in claim 8 wherein said visual read-out means includes a screen for a graphic display of said sequence of error signals over the time of the treatment.

11. In combination
a scale for weighing a patient undergoing a change in weight treatment said scale having means for emitting an output signal corresponding to an actual weight of the patient; and
a weight monitoring system connected to said scale to receive said actual weight signal, said system including first means for generating a signal corresponding to an amount of weight change of the patient over a period of time, second means for generating a signal corresponding to the lapse of time within said period of time, and a visual read-out means for displaying said signals, said read-out means including a first linear display for chronologically displaying an actual change in weight of the patient at a given time in bar form and a second linear display parallel to and said first linear display for continuously displaying the elapsed time in bar form.

12. A method of monitoring the weight of a patient undergoing a change in weight treatment, said method comprising the steps of
generating a first signal corresponding to an actual change in weight of the patient at predetermined intervals of time during the treatment;
generating a second signal corresponding to an elapse of time of the treatment; and
displaying said signals in bar form and in parallel relation to obtain a visual comparison of the change in weight relative to the elapsed time.

13. A method as set forth in claim 12 wherein each signal is continuously displayed during the time of treatment.

14. A method of monitoring the weight of a patient undergoing a change in weight, said method comprising the steps of
generating a first signal corresponding to an actual weight of the patient at predetermined intervals of time during treatment;
generating a second signal corresponding to a desired weight change;
generating a third signal corresponding to a period of time for the desired weight change;
delivering a programmed weight signal from said second and third signals corresponding to a desired weight for the patient at each said interval of time;
comparing said first signal with said programmed weight signal at each interval of time to obtain an error signal in response to a difference between said first signal and said programmed weight signal; and
graphically displaying a chronological sequence of said error signals.

15. A method as set forth in claim 14 which further comprises the steps of withdrawing fluids from the patient to effect a programmed weight loss in the patient during the treatment and of adjusting the rate of withdrawal in response to said error signals.

16. A method as set forth in claim 15 wherein said rate of withdrawal is automatically adjusted in response to said error signals.

* * * * *

UNITED STATES PATENT AND TRADEMARK OFFICE
CERTIFICATE OF CORRECTION

PATENT NO. : 4,629,015

DATED : December 16, 1986

INVENTOR(S) : Peter Fried and Burt L. Swersey

It is certified that error appears in the above-identified patent and that said Letters Patent is hereby corrected as shown below:

Column 9, line 9 after "period of time" insert -, a comparator for comparing the actual weight signal with the programmed weight signal to produce an error signal in response to a difference therebetween, and a visual read-out means for graphically displaying a chronological sequence of said error signals- Signed and Sealed this Thirty-first Day of January, 1989

Attest:

DONALD J. QUIGG

*Attesting Officer*   Commissioner of Patents and Trademarks